United States Patent [19]
Frantzen

[11] Patent Number: 5,931,866
[45] Date of Patent: Aug. 3, 1999

[54] RADIALLY EXPANDABLE STENT FEATURING ACCORDION STOPS

[76] Inventor: John J. Frantzen, 424 Poker Flat Rd., Copperopolis, Calif. 95228

[21] Appl. No.: 09/028,305

[22] Filed: Feb. 24, 1998

[51] Int. Cl.$^6$ ........................................................ A61F 2/06
[52] U.S. Cl. ................................................................ 623/1
[58] Field of Search ....................................... 623/1, 11, 12

[56] References Cited

U.S. PATENT DOCUMENTS

| | | |
|---|---|---|
| D. 380,266 | 6/1997 | Boatman et al. . |
| D. 380,831 | 7/1997 | Kavteladze et al. . |
| 5,133,732 | 7/1992 | Wiktor . |
| 5,139,480 | 8/1992 | Hickle et al. . |
| 5,195,984 | 3/1993 | Schatz . |
| 5,242,399 | 9/1993 | Lau et al. . |
| 5,314,444 | 5/1994 | Gianturco . |
| 5,421,955 | 6/1995 | Lau et al. . |
| 5,425,739 | 6/1995 | Jessen . |
| 5,441,515 | 8/1995 | Khosravi et al. . |
| 5,443,477 | 8/1995 | Marin et al. . |
| 5,485,667 | 1/1996 | Kleshinski . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,554,181 | 9/1996 | Das . |
| 5,562,641 | 10/1996 | Flomenblit et al. . |
| 5,578,149 | 11/1996 | DeScheerder et al. . |
| 5,591,195 | 1/1997 | Taheri et al. . |
| 5,591,197 | 1/1997 | Orth ........................................ 606/198 |
| 5,591,223 | 1/1997 | Lock et al. . |
| 5,591,226 | 1/1997 | Trerotola et al. . |
| 5,591,230 | 1/1997 | Horn et al. . |
| 5,603,721 | 2/1997 | Lau et al. . |
| 5,605,530 | 2/1997 | Fischell et al. . |
| 5,607,445 | 3/1997 | Summers . |
| 5,618,299 | 4/1997 | Khosravi et al. . |
| 5,624,411 | 4/1997 | Tuch . |
| 5,630,840 | 5/1997 | Mayer . |
| 5,632,763 | 5/1997 | Glastra . |
| 5,634,941 | 6/1997 | Winston et al. . |
| 5,637,113 | 6/1997 | Tartaglia et al. . |
| 5,697,971 | 12/1997 | Fischell ....................................... 623/1 |
| 5,776,161 | 7/1998 | Globerman ............................. 606/194 |
| 5,807,404 | 9/1998 | Richter ........................................ 623/1 |
| 5,810,872 | 9/1998 | Kanesaka ................................. 606/198 |
| 5,824,056 | 10/1998 | Rosenberg ................................. 623/1 |
| 5,827,321 | 10/1998 | Roubin ................................... 606/195 |
| 5,836,966 | 11/1998 | St. Germain ............................ 606/198 |

FOREIGN PATENT DOCUMENTS

679372 A2  11/1995  European Pat. Off. .

*Primary Examiner*—Michael J. Milano
*Attorney, Agent, or Firm*—Heisler & Associates

[57] ABSTRACT

A radially expandable surgical stent is provided with a helical element 20 extending from a first end 12 of the stent 10 to a second end 14 of the stent 10 with a series of turns 26. Each turn 26 of the helical element 20 includes bends 30, 32, 34 therein which can have their radius of curvature 35 increased to expand the stent 10 radially. The stent 10 resists an accordion effect caused when axial contracting forces are applied to the stent, by having axial elements 50 between turns 26 in the helical element 20. The axial elements 50 span gaps 44 between adjacent turns 26 and maintain a spacing between the turns 26.

18 Claims, 3 Drawing Sheets

RADIALLY EXPANDABLE STENT FEATURING ACCORDION STOPS

FIELD OF THE INVENTION

The following invention relates to stents for implantation into a body lumen such as an artery which can be radially expanded after implantation to support the body lumen. More particularly, this invention relates to stents which include a helical element extending helically from a first end of the stent to a second end of the stent and which exhibit both radial expandability and flexibility.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Radially expandable surgical stents are known in the art which are formed from a single helical element and which exhibit desirable radial expandability characteristics and also readily flex when passed along a curving body lumen. One such stent is described in U.S. Pat. No. 5,591,230 to Horn. While the Horn stent exhibits desirable flexibility and radial expandability characteristics it is subject to axial contraction when compressive loads are experienced. For instance, when the Horn prior art stent is in a radially collapsed configuration and is passing through a body lumen, if leading portions of the stent temporarily catch against walls of the body lumen the trailing portions of the stent can be caused to collapse axially toward the leading edge a significant amount.

Such axial contraction resulting from axial loads is referred to as an accordion effect. This axial contraction is distinct from axial contraction exhibited by many stents when they are being radially expanded within a body lumen but under no axially compressive load. This accordion effect is undesirable in that it can make the stent more difficult to position precisely within the body lumen.

Additionally, if the accordion effect occurs to a great extent or while the stent is flexed and has a central axis thereof bent, there is an opportunity for adjacent turns in the helical element to bind together. This binding can sometimes cause breakage of the stent elements or permanent deformation of the stent in an undesirable manner. Accordingly, a need exists for a single helical element surgical stent which resists the accordion effect while still being radially expandable and while still having sufficient flexibility to follow tortuous pathways within a body lumen.

SUMMARY OF THE INVENTION

This invention provides a surgical stent having a helical element extending from a first end of the stent to a second end of the stent. The helical element passes through multiple turns as it extends around the central axis and maintains a substantially constant distance away from the central axis. A series of bends are provided on each turn of the helical element including valley bends and peak bends. The bends are joined together by segments. Adjacent segments can rotate slightly about the bends in a manner causing a cylindrical contour of the stent to be radially expanded away from the central axis.

Gaps are provided between each turn in the helical element. To resist the accordion effect and maintain the gaps between the adjacent turns in the helical element, axial elements are provided as accordion stops. Each axial element extends between adjacent turns in the helical element and spans the gap to maintain the gap between the adjacent turns in the helical element. The axial elements allow the stent to still be flexed and have its central axis bend but substantially prevents the accordion effect and assists in maintaining an overall axial length of the stent.

OBJECTS OF THE INVENTION

Accordingly, a primary object of the present invention is to provide a radially expandable surgical stent which is configured from a helical element with multiple turns but which resists an accordion effect tending to cause the stent to shrink axially when axial loads are encountered by the stent.

Another object of the present invention is to provide a radially expandable surgical stent which exhibits a high degree of flexibility.

Another object of the present invention is to provide a surgical stent which can be easily located at a desired location within a body lumen during a surgical procedure and easily radially expanded to support the body lumen.

Another object of the present invention is to provide a surgical stent formed from materials compatible with an implantation environment.

Another object of the present invention is to provide a flexible radially expandable surgical stent which resists the accordion effect while maintaining flexibility and radial expandability characteristics.

Other further objects of the present invention will become apparent from a careful reading of the included drawing figures, the claims and detailed description of the invention.

DESCRIPTION OF THE PREFERRED EMBODIMENT

Figure 1:
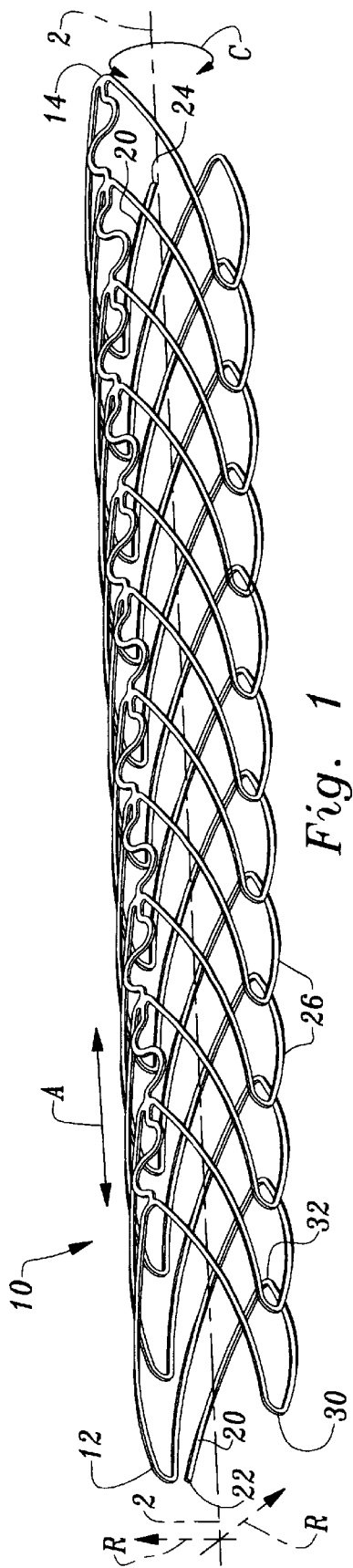
FIG. 1 is a perspective view of the stent of this invention with a single helical element extending from a first end of the stent to a second end of the stent and with axial elements located between adjacent turns of the helical element to resist the accordion effect.
Figure 2:
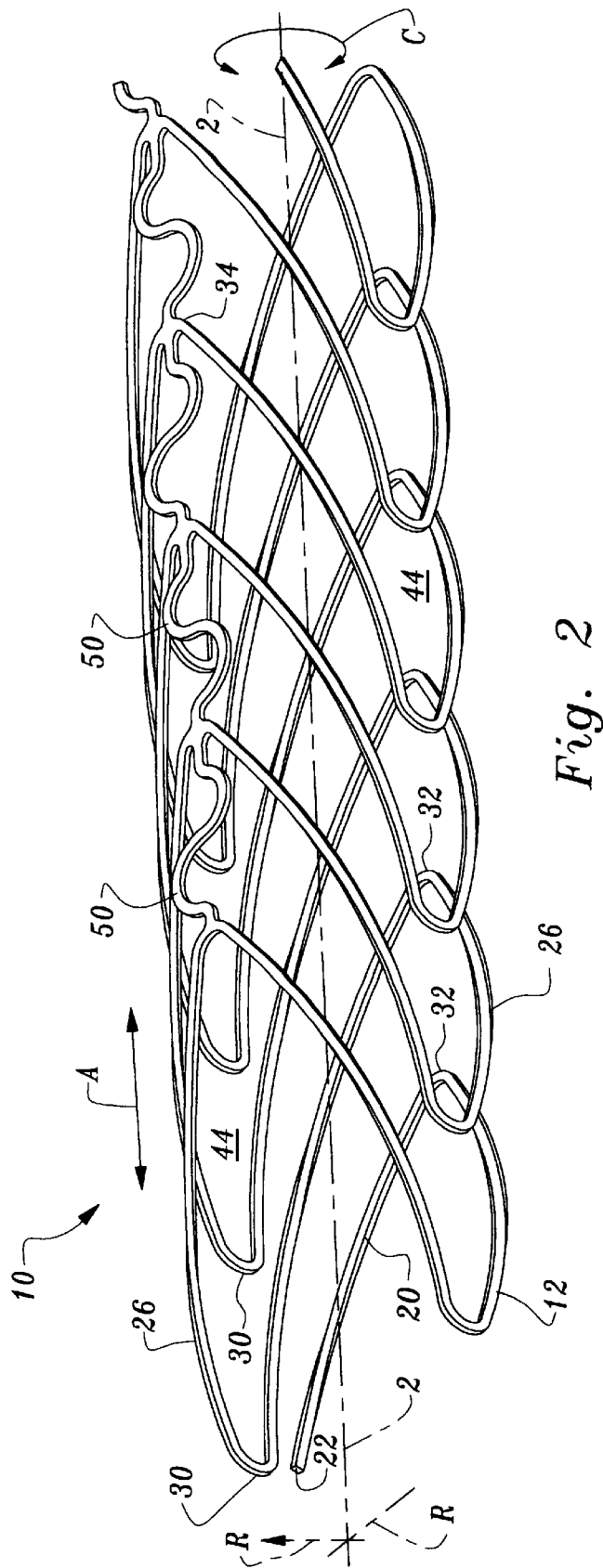
FIG. 2 is a perspective view of a portion of that which is shown in FIG. 1 revealing the configuration of the stent of this invention in greater detail.

Referring to the drawings wherein like reference numerals represent like parts throughout the various drawing figures, reference numeral 10 is directed to a radially expandable surgical stent which has a generally cylindrical contour spaced a constant radial distance away from a central axis 2 (FIGS. 1 and 2). The stent 10 can be radially expanded along arrow R to support a body lumen, such as an artery, during a surgical procedure. Axial contraction due to axial forces along arrow A (FIG. 1), resulting in a so-called "accordion effect," are resisted by having axial elements 50 spanning gaps 44 between adjacent turns 26 in a helical element 20 forming the cylindrical contour of the stent 10.

Figure 3:
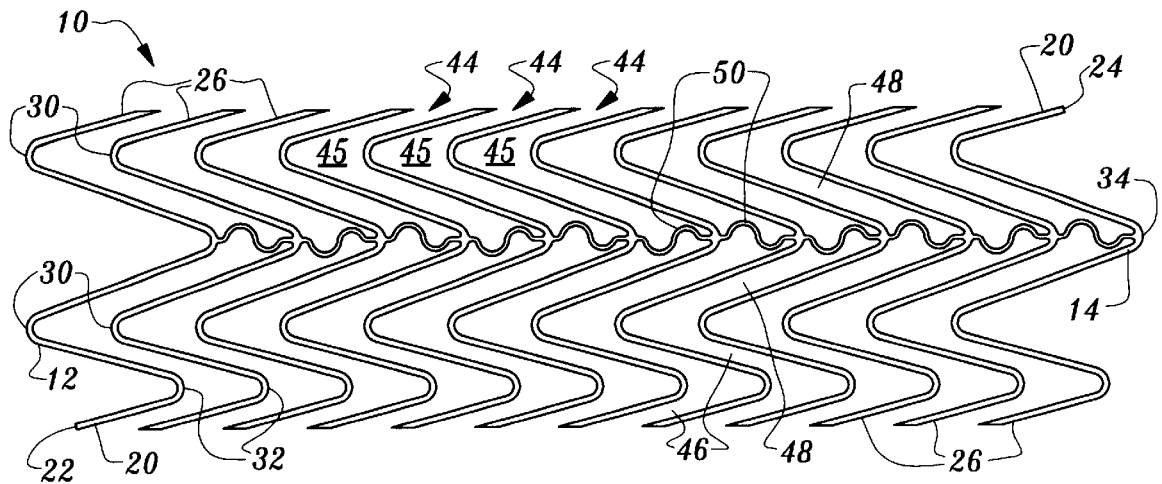
FIG. 3 is a cylindrical projection of that which is shown in FIG. 1.
Figure 4:
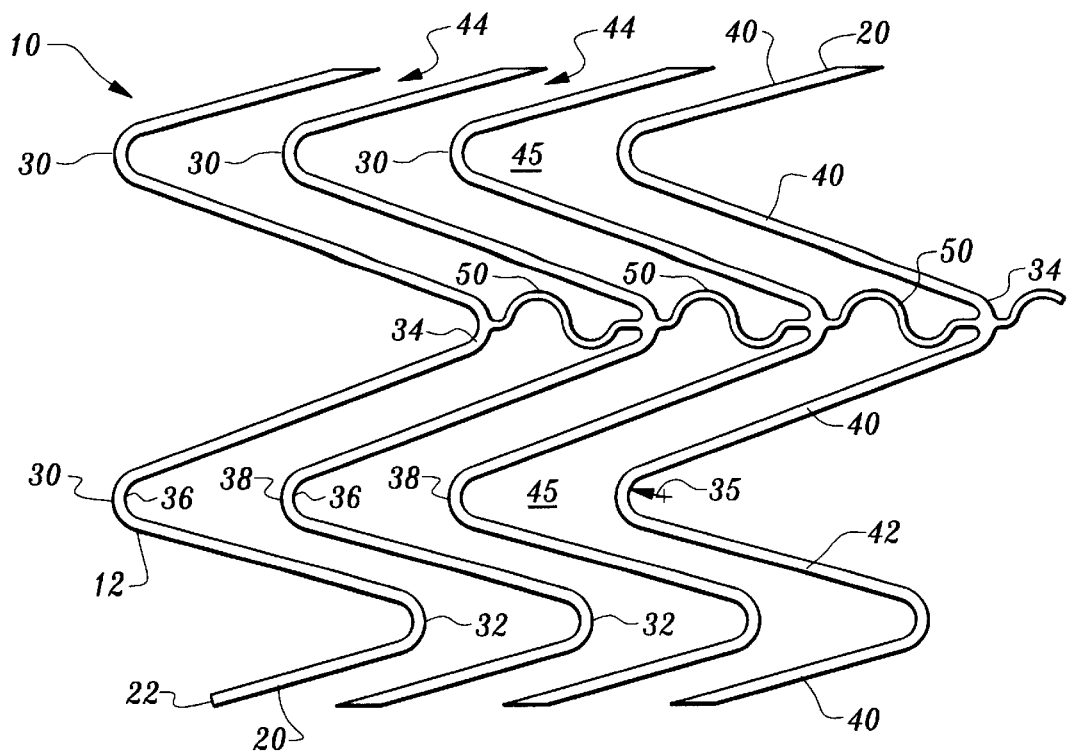
FIG. 4 is a cylindrical projection of a portion of that which is shown in FIG. 3 magnified to reveal details of the configuration of the stent.
Figure 5:
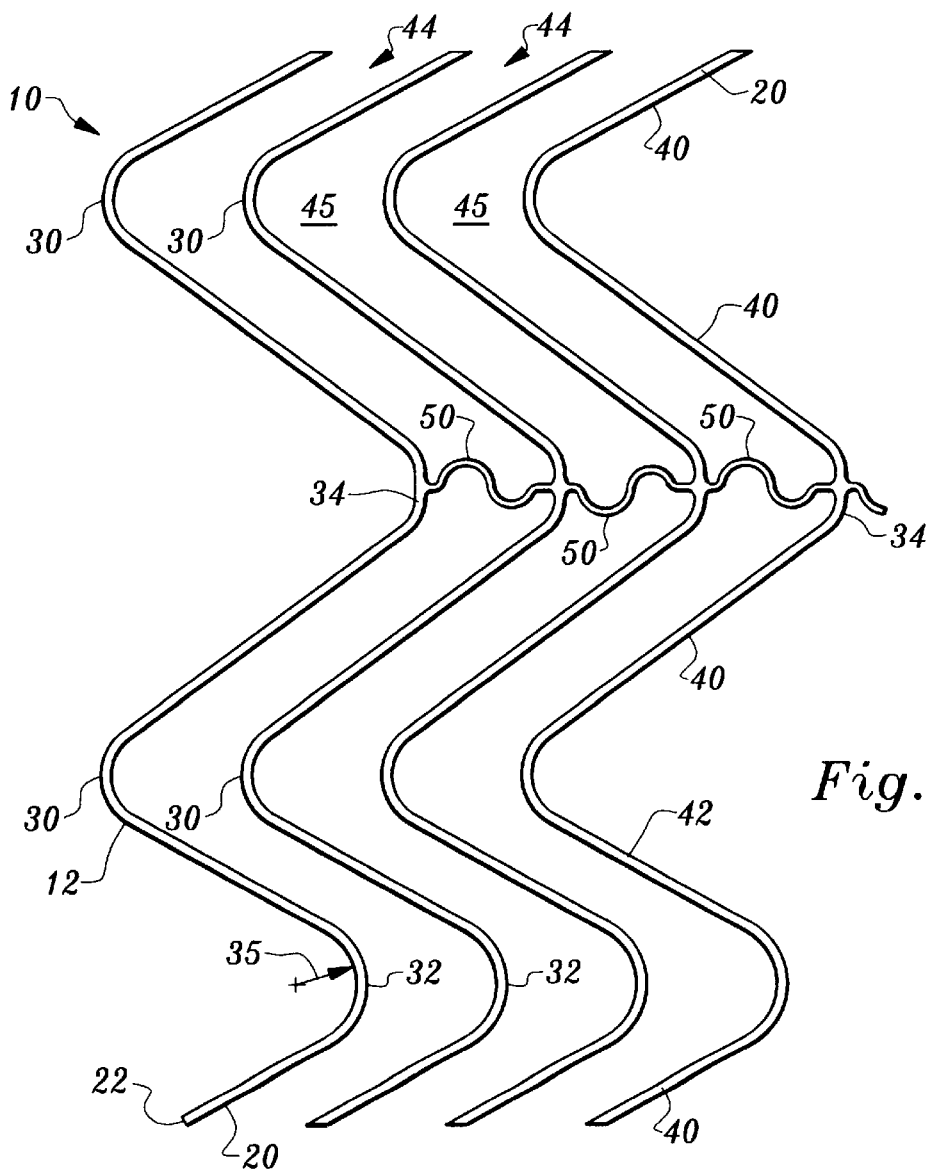
FIG. 5 is a cylindrical projection of that which is shown in FIG. 4 after radial expansion of the stent.

In essence, and with particular reference to FIGS. 1–3, the stent 10 exhibits the following basic configuration. A helical element 20 extends helically from the first end 12 of the stent 10 to the second end 14 of the stent 10. The helical element 20 includes a series of turns 26, each turn defined by 360 degrees of rotation of the helical element 20 about the central axis 2 in a circumferential direction along arrow C (FIGS. 1 and 2). The helical element 20 has bends therein including valley bends 30, low peak bends 32 and high peak bends 34. Long segments 40 (FIG. 4) and short segments 42 extend between adjacent bends 30, 32, 34. A gap 44 is provided between each turn 26 of the helical element 20. The gap 44 is maintained and the accordion effect prevented by including axial elements 50 extending between adjacent turns 26 in the helical element 20.

More specifically, and with particular reference to FIGS. 1–5, details of the helical element 20 are described. The helical element 20 preferably is formed from a common material with other portions of the stent, such as 316 stainless steel, which is appropriately bio-compatible and exhibits desired elasticity characteristics. The helical element 20 preferably extends from the first end 12 of the stent 10 to the second end 14 of the stent 10. Alternatively, multiple helical elements could form the cylindrical contour of the stent 10. Either the multiple helical elements could each extend between the ends 12, 44 of the stent 10 or some of the helical elements could start and stop at intermediate locations between the ends 12, 14 of the stent 10.

The helical element 20 preferably has a constant radial thickness of 0.006 inches and has a constant width between adjacent gaps 44 of 0.006 inches. These preferred dimensions for the helical element 20 correspond to a stent having an original diameter of 0.1 inches and a length of 1.09 inches. If a larger or smaller stent is to be formed, and if greater or lesser radial expansion forces are to be supplied or different loads encountered, the thickness and width of the helical element 20 would be appropriately adjusted. The helical element 20 extends from a first tip 22 adjacent the first end 12 to a second tip 24 adjacent the second end 14. Preferably, twelve turns are provided in the helical element 20 between the first tip 22 and the second tip 24. The helical element 20 preferably maintains a constant thickness and width along its entire length from the first tip 22 to the second tip 24.

The helical element 20 includes a series of bends including the valley bends 30, low peak bends 32 and high peak bends 34 as the helical element 20 extends around the cylindrical contour of the stent 10. These bends 30, 32, 34 provide one form of a means to allow the stent 10 to be expanded radially, along arrow R (FIG. 1), when the bends 30, 32, 34 are expanded. The valley bends 30 are those bends in each turn 26 of the helical element 20 which are closest to the first end 12 of the stent 10. Preferably, each turn 26 of the helical element 20 has two valley bends 30 therein. The two valley bends 30 in each turn 26 are a similar distance from the first end 12.

Each turn 26 of the helical element 20 also includes two peak bends including the low peak bend 32 and the high peak bend 34. Preferably, the low peak bend 32 is provided first as the helical element 20 extends from the first tip 22 to the second tip 24 and the high peak bend 34 is provided second. The low peak bend 32 and high peak bend 34 alternate with the valley bends 30 so that a uniform pattern is provided for each turn 26 of the helical element 20. Specifically, this pattern of bends 30, 32, 34 includes a low peak bend 32 adjacent the first tip 22, followed by a first valley bend 30, followed by a high peak bend 34, followed by a second valley bend 30, followed by the next turn 26 in the helical element 20. The next turn 26 would similarly have a low peak bend 32, followed by a first valley bend 30, followed by high peak bend 34, followed by a second valley bend 30.

The bends 30, 32, 34 within each turn 26 are spaced away from each other a common amount so that each of the low peak bends 32 in each turn 26 are aligned axially with each other, each high peak bend 34 of each turn 26 is aligned with other high peak bends 34 and each valley bend 30 of each turn 26 is aligned with other valley bends 30.

Each low peak bend 32 is closer to the valley bends 30 than the high peak bends 34. The valley bends 30 are spaced sufficiently away from the low peak bends 32 and high peak bends 34 and the gap 44 is sufficiently narrow that the low peak bends 32 and high peak bends 34 of the first turn 26 adjacent the first end 12 of the stent 10 are further from the first end 12 of the stent 10 than are the valley bends 30 of the second turn 26 away from the first end 12 of the stent 10. This overlapping feature between the bends 30, 32, 34 of adjacent turns 26 enhances an amount of support the stent 10 can provide to a body lumen when implanted therein.

Each of the bends 30, 32, 34 preferably has a radius of curvature 35 of approximately 0.02 inches and has a similar angular width between adjacent segments 40, 42 on opposite sides of each bend 30, 32, 34. However, the low peak bends 32 would typically have a slightly lesser angular displacement between segments 40, 42 on opposite sides of the low peak bends 32 than exist between segments 42 on opposite sides of the high peak bends 34.

Each bend 30, 32, 34 has a trough side 36 on an interior side thereof and a crest side 38 on an exterior side thereof.

In other words, a concave side of each bend 30, 32, 34 defines a trough 36 and a convex side of each bend 30, 32, 34 defines a crest 38. Each of the troughs 36 and each of the crests 38 in each turn 26 are preferably aligned axially with each other.

The long segments 40 on each turn 26 extend between the valley bends 30 and the high peak bend 34. Additionally, a long segment 40 extends from the second valley bend 30 to the low peak bend 32 of the next adjacent turn 26 as the helical element 20 extends from the first tip 22 to the second tip 24. One short segment 42 is provided for each turn 26 between the low peak bend 32 and the first valley bend 30 of each turn 26. Because more long segments 40 are provided for each turn 26 than are short segments 42, it can be seen that each turn 26 is offset away from the first end 12 a greater distance than previous turns 26. In this way, the helical element 20 extends helically from the first end 12 of the stent 10 to the second end 14 of the stent 10 with the gap 44 between adjacent turns 26.

The gap 44 has curves 45 adjacent each of the bends 30, 32, 34 which cause the gap 44 to have an undulating pattern as each gap 44 extends between each adjacent turn 26. While each gap 44 is considered to be separate from adjacent gaps 44 it is understood that in fact each gap 44 is joined to adjacent gaps 44 helically so that in fact one gap 44 extends from the first end 12 of the stent 10 to the second end 14 of the stent 10 as the helical element 40 extends from the first end 12 to the second end 14. However, for convenience and consistency in nomenclature, the stent 10 is consistently described as having separate gaps 44 between each adjacent turn 26 in the helical element 20.

A spacing between segments 40, 42 of adjacent turns 26 define a width of the gap 44. The gap 44 does not have a constant width. Rather, the gap 44 has wide portions 46 and narrow portions 48. The wide portions 46 extend between the valley bends 30 and the high peak bends 34 and the narrow portions 48 extend between the valley bends 30 and the low peak bends 32. Preferably, the wide portions 46 are 0.0214 inches and the narrow portions 48 are 0.016 inches.

While the gaps 44 maintain their width when the stent 10 is at rest, when axial forces along arrow A (FIG. 1) are encountered the gaps 44 can be narrowed. Narrowing of the gaps 44 is generally referred to as the accordion effect and causes an overall length of the stent 10 to be shortened. If the accordion effect is not resisted and continues until adjacent turns 26 of the helical element 20 touch each other and the gap 44 is closed, the adjacent turns 26 can bind together and cause fracture or undesirable deformation of the stent 10. To resist the accordion effect, axial elements 50 are interposed between adjacent turns 26 and spanning the gap 44.

Figure 6:
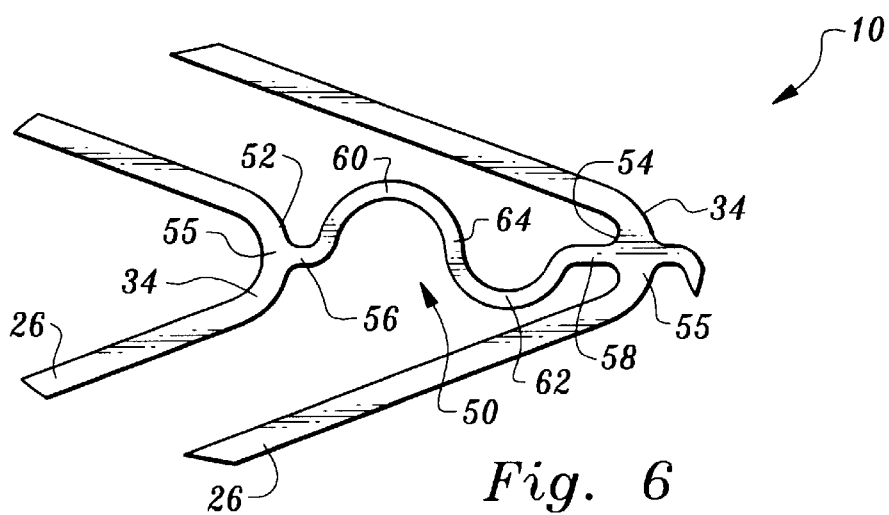
FIG. 6 is a cylindrical projection of a portion of that which is shown in FIG. 4 magnified to reveal details of the axial element which acts as an accordion stop providing resistance to the accordion effect.

With particular reference to FIG. 6, details of the axial elements 50 are provided. Each axial element 50 preferably is S-shaped and extends from a first extremity 52 to a second extremity 54. The first extremity 52 attaches to the adjacent helical element 20 through a junction 55. The second extremity 54 similarly attaches to the adjacent helical element 20 through another junction 55. Each junction 55 is preferably not a weld or other bond between separate elements 20, 50. Rather, the elements 20, 50 are preferably formed together as a unitary mass of material such as by utilizing a cutting tool to cut away the gaps 44 between the turns 26 of the helical element 20 and the axial elements 50, so that only the helical element 20 and the axial elements 50 remain.

Each axial element 50 preferably extends away from the first extremity 52 with a first leg 56 and extends away from the second extremity 54 with a second leg 58. The first leg 56 and second leg 58 are substantially linear and oriented along a common axial line. The first leg 56 and second leg 58 do not come into contact with each other. Rather, a large curve 60 is located adjacent the first leg 56 and a small curve 62 is located adjacent the second leg 58. An inflection point 64 joins the large curve 60 to the small curve 62. Preferably, the large curve 60 has a radius of curvature of 0.125 inches and the small curve 62 has a radius of curvature of 0.1 inches.

The axial elements 50 are located with the first extremity 52 attached to a high peak bend 34 and the second extremity 54 attached to a high peak bend 34 of the next adjacent turn 26 on an opposite side of the gap 44. By providing the small curve 62 with a smaller radius of curvature than the large curve 60, and by providing each curve 60, 62 with substantially 180 degrees of arc, the small curve 62 can avoid interference with the long segments 40 on each side of the high peak bend 34 and keep the axial elements 50 from touching the long segments 40. The curves 60, 62 give the axial elements 50 enhanced flexibility to allow the overall stent 10 to maintain flexibility. Additionally, the curves 60, 62 allow a minimal amount of the accordion effect to occur without damaging the axial elements 50 or other portions of the stent 10 but while maintaining the gaps 44 between adjacent turns 26 of the helical element 20. The axial elements 50 preferably have a width of 0.004 inches, two-thirds of a width of the helical elements 20.

Preferably, each gap 44 is spanned by an axial element 50 and each of the axial elements 50 are located at the high peak bends 34 of each turn 26 of the helical element 20. Accordingly, each of the axial elements 50 is aligned axially along a common line from the first end 12 of the stent 10 to the second end 14 of the stent 10 with such an axially aligned orientation the axial elements 50 together resist axial shortening of the stent 10 both when axial compression forces are experienced and when the stent 10 is radially expanded. Each axial element 50 is preferably rotated 180 degrees so that if the large curve 60 extends away from the first tip 22 in a circumferential direction along arrow C (FIG. 1) for one gap 44, than the next axial element 50 in an adjacent gap 44 will have its large curve 60 extending in a direction extending toward the first tip 22 of the helical element 20 in a circumferential direction.

While the axial elements 50 are preferably only connected to the high peak bends 34 and one axial element 30 is provided spanning each gap 44, other locations and numbers of axial elements 50 can be utilized in alternative embodiments of the stent 10. For instance, the axial elements 50 could be provided spanning every other gap 44 rather than every gap 44. The axial elements 50 could be located adjacent the high peak bends 34 spanning some gaps 44 and adjacent the low peak bends 32 or the valley bends 30 in other gaps 44. Also, axial elements 50 could be provided spanning the gaps 44 at locations spaced from the curves 45 in the gaps 44 and between segments 40, 42.

Also, the axial elements 50 can have a variety of different configurations other than the S-shaped configuration of the preferred embodiment. For instance, the axial elements could be linear or could be Z-shaped and zig zag from the first extremity to the second extremity rather than having the curves 60, 62 of the preferred embodiment.

In use and operation, the stent 10 is formed and utilized in the following manner. While the stent 10 could be formed using a variety of different known methods, the stent 10 is preferably formed initially from a hollow cylinder of stainless steel having a diameter of 0.1 inches. Such a diameter size when coupled with other dimensions disclosed herein has been found to be effective during prototyping and experimentation. However, this diameter and other dimensions of the stent 10 can be scaled, such as by increasing all of the dimensions proportionally to provide stents of differing sizes. For instance, when larger coronary arteries are designated for stent implantation the dimensions of the stent 10 would be scaled up to provide a stent with appropriate compressed and expanded diameters and strength. A cutting tool such as a numerically controlled laser cutter can then be utilized to cut away the gap 44 portions of the stent 10 and portions of the tube adjacent the first end 12 and second end 14 of the stent 10, until only the helical element 20 and axial elements 50 remain.

When the stent 10 is to be implanted within a body lumen, the stent 10 is typically placed upon a catheter which has an appropriate mechanism to exert radial pressure against the stent 10 to cause the stent 10 to expand radially. The stent 10 expands radially, along arrow R (FIG. 1) by having the bends 30, 32, 34 expand, rather than merely having the helical element 20 unwind helically. For maximum expansion, the stent 10 would be placed over this catheter and collapsed radially onto the catheter to a compressed diameter of approximately 0.06 inches. The stent 10 can then be located, utilizing the catheter, at a location in a body lumen, such as an artery, where implantation of the stent 10 is desired. The catheter then utilizes its expansion mechanism to radially expand the stent 10 from a compressed diameter of 0.06 inches to a desired expanded diameter. The expanded diameter can extend up to 0.2 inches or beyond depending on the particular needs of the patient and medical practitioner.

While the stent 10 is being located within the body lumen, should the stent 10 encounter obstacles which exert an axial force tending to compress the stent 10 axially, the axial elements 50 prevent the turns 26 of the helical element 20 from contacting each other and damaging the stent 10. Additionally, when tortuous arterial pathways are encountered by the stent 10 during implantation, the stent 10 can flex, but not to the point where adjacent turns 26 of the helical element 20 contact each other and bind together or cause undesirable deformation or fracture.

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure.

What is claimed is:

1. A surgical stent comprising in combination:
   at least one elongate helical element positioned to define at least a portion of a generally cylindrical contour for said stent;
   said helical element extending angularly more than 360 degrees around a central axis of said cylindrical contour of said stent, such that said helical element has at least two turns, each turn spaced axially from adjacent turns by a gap;
   at least one axial element having at least two extremities including a first extremity and a second extremity, said first extremity attached to said helical element on a first turn of said at least two turns and said second extremity attached to said helical element on a second turn of said at least two turns, such that said axial element spans said gap;
   wherein said at least one axial element is S-shaped including two curves facing in opposite directions between said first extremity and said second extremity, said two curves joined together at an inflection point; and
   wherein said two curves include a smaller curve and a larger curve, said smaller curve having a radius of curvature less than a radius of curvature of said larger curve, said smaller curve adjacent said second extremity, said second extremity attached to a trough side of one of said bends in said helical element and said first extremity attached to a crest side of one of said bends in said helical element.

2. The stent of claim 1 wherein said stent includes means to allow said stent to have its cylindrical contour expanded radially away from said central axis.

3. The stent of claim 2 wherein said radial expansion means maintains an angular extension of said helical element about said central axis at a constant amount before, during and after radial expansion of said cylindrical contour of said stent.

4. The stent of claim 3 wherein said radial expansion means includes said elongate helical element having a series of bends therein with at least two bends in said helical element for every turn in said helical element, said bends oriented to cause said helical element to elongate circumferentially when said bends have a radius of curvature thereof increased.

5. The stent of claim 1 wherein said elongate helical element includes a series of bends therein, each bend spaced away from adjacent bends by segments, said helical element including at least two bends in each said turn of said helical element, at least a portion of each pair of adjacent turns in said helical element overlapping each other axially while said adjacent turns are spaced away from each other circumferentially with said gap maintained between said adjacent turns.

6. The stent of claim 5 wherein each said turn has a common number of bends therein, said bends in each said turn aligned axially with said bends of said adjacent turns, such that said bends in said adjacent turns are in phase with each other.

7. The stent of claim 1 wherein said elongate helical element includes a series of bends therein, each said turn in said elongate helical element including at least two bends, and said extremities of said at least one axial element are each attached to said helical element at one of said bends.

8. The stent of claim 7 wherein each said gap between said adjacent turns is spanned by at least one said axial element, each said axial element aligned axially, such that said axial elements resist axial contraction of said stent when said stent is radially expanded.

9. A surgical stent featuring radial expandability and limited axial contraction when expanded radially, the stent comprising in combination:
   a cylindrical contour having a constant inner radius from a central axis and a constant outer radius from said central axis;
   a series of at least two helical gaps passing through said cylindrical contour from said inner radius to said outer radius, each said helical gap spaced axially from adjacent helical gaps by a helical element having at least three turns about said central axis and each said helical gap spaced helically from said adjacent helical gaps by at least one axial element having at least two extremities including a first extremity and a second extremity, said at least one axial element extending between two of said turns in said helical element adjacent each said gap;

wherein said at least one axial element is S-shaped including two curves facing in opposite directions between said first extremity and said second extremity, said two curves joined together at an inflection point; and wherein said two curves include smaller curve and a larger curve, said smaller curve having a radius of curvature less than a radius of curvature of said larger curve, said smaller curve adjacent said second extremity, said second extremity attached to a trough side of one of said bends in said helical element and said first extremity attached to a crest side of one of said bends in said helical element.

10. The stent of claim 9 wherein said helical element and said axial elements each have a similar constant radial thickness and are formed from a unitary mass.

11. The surgical stent of claim 10 wherein said helical element has a constant width between said adjacent helical gaps.

12. The surgical stent of claim 11 wherein only one helical element extends from a first end of said stent to a second end of said stent, said helical element having at least three turns.

13. The surgical stent of claim 12 wherein said helical element includes at least two bends in each turn of said helical element, said axial elements connected to said helical element at said bends, said bends including means to flex and adjust a radius of curvature of said bends.

14. A flexible radially expandable surgical stent comprising in combination:

at least one elongate helical element extending helically from a first end of said stent to a second end of said stent within a cylindrical contour a substantially constant distance from a central axis of said stent;

said helical element having at least two turns as said helical element extends from said first end to said second end;

at least one axial element having at least two extremities including a first extremity and a second extremity, said at least one axial element extending between two of said at least two turns which are adjacent to each other;

wherein said at least one axial element is S-shaped including two curves facing in opposite directions between said first extremity and said second extremity, said two curves joined together at an inflection point; and wherein said two curves include a smaller curve and a larger curve, said smaller curve having a radius of curvature less than a radius of curvature of said larger curve, said smaller curve adjacent said second extremity, said second extremity attached to a trough side of one of said bends in said helical element and said first extremity attached to a crest side of one of said bends in said helical element.

15. The stent of claim 14 wherein said axial element includes sufficient length and rigidity to prevent said adjacent turns from coming into contact with each other.

16. The stent of claim 14 wherein at least two bends are included in each turn of said helical element, said bends spaced apart by segments, at least one of said segments in each said turn oriented to position at least one said bend in each said turn at a location which axially overlaps at least one said bend in each adjacent said turn while maintaining a gap between said adjacent turns, said bends including means to flex to adjust a radius of curvature of said bends and radially expand said cylindrical contour of said stent.

17. The stent of claim 16 wherein said segments between said bends are substantially linear, said segments having sufficient length to allow a diameter of said cylindrical contour of said stent to be doubled while maintaining at least one of said bends in each said turn at a location overlapping at least one said bend of adjacent said turns.

18. The stent of claim 14 wherein a gap between adjacent said turns of said helical element is spanned by at least one said axial element, each said axial element spaced circumferentially no more than 360 degrees from adjacent said axial elements.

* * * * *